(12) United States Patent
Almering et al.

(10) Patent No.: US 11,505,512 B2
(45) Date of Patent: Nov. 22, 2022

(54) CO-PRODUCTION OF HIGH PURITY ISOBUTANE AND BUTENE-1 FROM MIXED C4S

(71) Applicant: LUMMUS TECHNOLOGY LLC, Bloomfield, NJ (US)

(72) Inventors: Martinus Johannes Almering, Houston, TX (US); Rosette Barias, Spring, TX (US); Romain Lemoine, Houston, TX (US); Michael Jon Scott, Houston, TX (US)

(73) Assignee: LUMMUS TECHNOLOGY LLC, Bloomfield, NJ (US)

( * ) Notice: Subject to any disclaimer, the term of this patent is extended or adjusted under 35 U.S.C. 154(b) by 247 days.

(21) Appl. No.: 17/064,009

(22) Filed: Oct. 6, 2020

(65) Prior Publication Data
US 2021/0101851 A1 Apr. 8, 2021

Related U.S. Application Data (60) Provisional application No. 62/911,541, filed on Oct. 7, 2019.

(51) Int. Cl.
*C07C 2/08* (2006.01)
*C07C 41/06* (2006.01)
(Continued)

(52) U.S. Cl.
CPC .............. *C07C 2/08* (2013.01); *B01J 19/245* (2013.01); *B01J 19/2445* (2013.01); *C07C 4/04* (2013.01); *C07C 4/06* (2013.01); *C07C 7/11* (2013.01); *C07C 41/06* (2013.01); *C07C 41/38* (2013.01); *B01J 2219/0004* (2013.01); *B01J 2219/00038* (2013.01); *C07C 2/86* (2013.01); *C07C 2/862* (2013.01); *C07C 2/864* (2013.01); *C07C 2/865* (2013.01)

(58) Field of Classification Search
CPC .... C07C 2/08; C07C 4/04; C07C 4/06; C07C 7/11; C07C 41/06; C07C 41/38; C07C 2/86; C07C 2/862; C07C 2/864; C07C 2/865; C07C 7/14891; C07C 29/80; B01J 19/2445; B01J 19/245; B01J 2219/00038; B01J 2219/0004; B01J 8/04; B01J 2208/0053; B01J 8/067; B01J 8/065; Y02P 20/10
See application file for complete search history.

(56) References Cited

U.S. PATENT DOCUMENTS

| | | | |
|---|---|---|---|
| 4,718,986 A | | 1/1988 | Comiotto et al. |
| 4,797,133 A | * | 1/1989 | Pujado .............. C10L 1/023 44/449 |

(Continued)

FOREIGN PATENT DOCUMENTS

| | | |
|---|---|---|
| CN | 102992933 A | 3/2013 |
| KR | 10-1987-0001082 B1 | 6/1987 |

OTHER PUBLICATIONS

International Search Report issued in PCT/US2020/054364 dated Jan. 27, 2021 (4 pages).

*Primary Examiner* — Ali Z Fadhel
(74) *Attorney, Agent, or Firm* — Osha Bergman Watanabe & Burton LLP (57) ABSTRACT

Systems and processes disclosed may be used to produce a high purity isobutane stream and a high purity 1-butene stream from mixed C4 streams having disparate starting compositions.

12 Claims, 4 Drawing Sheets

(51) Int. Cl.
*C07C 7/11* (2006.01)
*C07C 41/38* (2006.01)
*C07C 4/04* (2006.01)
*B01J 19/24* (2006.01)
*C07C 4/06* (2006.01)
*C07C 2/86* (2006.01)

(56) References Cited

U.S. PATENT DOCUMENTS

| | | | |
|---|---|---|---|
| 5,321,163 A | 6/1994 | Hickey et al. | |
| 5,628,880 A | 5/1997 | Hearn et al. | |
| 10,053,438 B2* | 8/2018 | Bolz | C07C 41/09 |
| 10,053,440 B2* | 8/2018 | Bolz | C07C 5/32 |
| 10,774,020 B2* | 9/2020 | Di Girolamo | C07C 7/163 |
| 2008/0021255 A1* | 1/2008 | Santiago-Fernandez | C07C 7/14891 |
| | | | 585/834 |
| 2008/0300439 A1* | 12/2008 | Di Girolamo | C07C 7/06 |
| | | | 585/639 |
| 2009/0253942 A1* | 10/2009 | Di Girolamo | C07C 41/06 |
| | | | 568/697 |
| 2012/0010451 A1 | 1/2012 | Di Girolamo et al. | |

* cited by examiner

CO-PRODUCTION OF HIGH PURITY ISOBUTANE AND BUTENE-1 FROM MIXED C4S

FIELD OF THE DISCLOSURE

Embodiments herein relate to processes and systems for the co-production of isobutane and 1-butene.

BACKGROUND

Various processes have been disclosed to produce a high purity isobutene stream from a mixed C4 stream. Many of these include the etherification of isobutene to produce methyl tert butyl ether (MTBE), which may be separated from the remaining C4s and then back cracked to form a pure isobutene stream. Such processes may be disclosed, for example, in U.S. Pat. Nos. 5,628,880 and 5,321,163, among others.

The separation of the isobutene in the form of MTBE allows the separation and recovery of butenes (1-butene and 2-butene).

SUMMARY OF THE DISCLOSURE

To the inventor's knowledge, no prior process has been provided for co-production of a high purity isobutane stream and a high purity 1-butene stream.

In one aspect, embodiments herein are directed toward a process for the co-production of high purity isobutane and high purity 1-butene streams. The process may include providing a first mixed C4 stream and a second mixed C4 stream, each comprising isobutene, isobutane, 1-butene, and 2-butene, and wherein the first mixed C4 stream has a higher concentration of isobutane than the second mixed C4 stream. The first mixed C4 stream and methanol, as a reactant or selectivator, may be fed to a first reaction system for converting isobutene contained therein to methyl tert butyl ether or isobutene dimers. The second mixed C4 stream and methanol, as a reactant or selectivator, may be fed to a second reaction system for converting isobutene contained therein to methyl tert butyl ether or isobutene dimers. The process may then include separating an effluent from the first reaction system in a first separation system, including a water wash system, to recover a first lights stream comprising 1-butene, 2-butene, isobutane, a first methanol+water stream, and a first heavy stream comprising the methyl tert butyl ether or the isobutene dimers. Further, the method includes separating an effluent from the second reaction system in a second separation system, including a water wash system, to recover a second lights stream comprising 1-butene, 2-butene, and isobutane, a second methanol+water stream, and a second heavy stream comprising the methyl tert butyl ether or the isobutene dimers. The first and second methanol+water streams may then be fed to a methanol recovery system to separate methanol from the water and returning at least a portion of the methanol to either or both the first and second reaction systems. The second lights stream may be fed to a separation system for recovering an isobutane containing stream, a 1-butene stream, and a first heavy C4 stream comprising n-butanes and 2-butene. The isobutane containing stream and the first lights stream may be fed to a separation system for recovering an isobutane stream and a second heavy C4 stream comprising n-butanes and 2-butene.

In another aspect, embodiments disclosed herein relate to a system for the co-production of high purity isobutane and high purity 1-butene streams. The system may include a first mixed C4 feed stream and a second mixed C4 feed stream, each comprising isobutene, isobutane, 1-butene, and 2-butene. The first mixed C4 stream may have a higher concentration of isobutane than the second mixed C4 stream. The system also includes a first methanol feed stream and a second methanol feed stream. A first reaction system is configured to receive the first mixed C4 stream and the first methanol stream and to react the first mixed C4 stream and methanol, as a reactant or selectivator, converting isobutene contained therein to methyl tert butyl ether or isobutene dimers. A second reaction system is configured to receive the second mixed C4 stream and the second methanol stream and to react the second mixed C4 stream and methanol, as a reactant or selectivator, converting isobutene contained therein to methyl tert butyl ether or isobutene dimers. The system further includes a first separation system, including a water wash system, for separating an effluent from the first reaction system to recover a first lights stream comprising 1-butene, 2-butene, isobutane, a first methanol+water stream, and a first heavy stream comprising the methyl tert butyl ether or the isobutene dimers, as well as a second separation system, including a water wash system, for separating an effluent from the second reaction system to recover a second lights stream comprising 1-butene, 2-butene, isobutane, a second methanol+water stream, and a second heavy stream comprising the methyl tert butyl ether or the isobutene dimers. A common methanol recovery system is provided for receiving the first and second methanol+water streams to separate methanol from the water and a flow line for returning at least a portion of the methanol to either or both the first and second reaction systems; a first lights separation system for receiving the second lights stream and recovering an isobutane containing stream, a 1-butene stream, and a first heavy C4 stream comprising n-butanes and 2-butene. A second lights separation system is configured for receiving the first lights stream and for recovering an isobutane stream and a second heavy C4 stream comprising n-butanes and 2-butene.

Other aspects and advantages will be apparent from the following description and the appended claims.

DETAILED DESCRIPTION

Embodiments herein relate to processes and systems for the co-production of isobutane and 1-butene. More specifically, embodiments herein are directed toward the production of high purity isobutane and 1-butene streams from mixed C4 streams. Even more specifically, embodiments herein are directed toward the concurrent production of high purity 1-butene and isobutane streams from a mixed C4 feedstock coming from an RFCC/FCC and/or steam cracker unit (SCU).

Various upstream production processes may be used to generate C4 streams, such as fluid catalytic cracking (FCC) units, resid fluid catalytic cracking units (RFCC), steam crackers, pyrolysis units (thermal cracking with or without steam), and various other methods of producing mixed C4s. The mixed C4 streams produced from these units may include isobutene, isobutane, 1-butene, 2-butene, n-butane, and butadienes, among other components.

While producing similar chemical compounds, these upstream C4 producing systems result in streams having different compositional mixtures of the various C4 compounds. For example, FCC or RFCC mixed C4s may have a much higher concentration of isobutane (>20 wt % or >25 wt %, for example) than a Raffinate-1 recovered from a steam cracker butadiene production process (<5 wt % or <3 wt % isobutane, for example). At the same time, the concentration of isobutylene in the FCC/RFCC C4s is much lower than for steam cracker C4s, (such as <25 or 30 wt % for RFCC vs. >35 or 40 wt % for steam cracker C4s). Likewise, each (FCC/RFCC vs. steam cracker) may have a difference in the concentration of 1-butene (such as less than 20 or 15 wt % vs. greater than 35 or 40 wt %). Further, the diene content of the FCC/RFCC mixed C4s is much higher than for the steam cracker Raffinate-1 (such as 0.3 wt % or 3,000 ppmw vs. 40 ppmw).

Desiring to separate the mixed C4s into various product streams, such as an isobutane stream and a 1-butene stream, one skilled in the art may simply mix each of the various C4 streams for co-processing. However, the present inventors have found that, based on the differences in composition between the streams, these feedstocks should be processed separately in parallel reaction trains, including common equipment integrating the reaction trains, to yield the desired high purity isobutane and high purity 1-butene products. Using the parallel reaction trains provides for recovery of Raffinate-2 streams, mixed C4 streams with isobutene effectively removed, from each reaction train, and allows an operator to optimize the sizing of equipment and associated utility consumption required for the isobutane and 1-butene purification. The raffinate-2 from the FCC/RFCC reaction train will have a relatively higher concentration of isobutane and a lower concentration of 1-butene. By comparison, the raffinate-2 from the steam cracker reaction train will have a much higher concentration of 1-butene and a lower concentration of isobutane.

In both reaction trains, isobutylene may be removed from the individual raffinate-2 streams through dimerization and/or conversion to methyl tert butyl ether in the reaction trains (as used herein, Train 1=FCC/RFCC C4 conversion, while Train 2=steam cracker C4 conversion). The reactor configuration in each train may be specific to the upstream C4 feed provided, tailored to meet the needs for converting the isobutylene. Further, it has been found that appropriate integration of product separations may provide for a high purity isobutane stream. Even though the steam cracker C4 feed has a comparatively low isobutane content, the additional isobutanes added to the FCC/RFCC raffinate streams provides for a high purity isobutane product stream.

When the reaction system produces iso-octene (isobutene dimers), the iso-octene produced in both reaction trains may be combined, purified to remove oxygenates, and then sent to a saturation reactor to convert the iso-octene to iso-octane, if desired. The isobutene dimers may alternatively be used for alkylation. When the reaction system produces methyl tert butyl ether (MTBE), the MTBE may be back-cracked to form a high purity isobutene stream, for example.

The reactor trains (Train 1 and Train 2) may each use methanol as a reactant (to produce MTBE) or as a selectivator (for selective dimerization). The raffinate streams from each reactor train may be separately water washed to remove the methanol. The resulting water/methanol streams may then be fed to a common methanol recovery system to provide for methanol recycle and wash water recycle.

As noted above, the configuration of the reactor trains may be designed to provide efficiencies based on the C4 supply to the individual train. For example, a reactor train having a higher initial concentration of isobutene may be processed in a fixed bed reactor or a series of fixed bed reactors, and may include an intermediate separation stage to remove a portion of the product (MTBE or dimer), thereby providing additional driving force for the continued conversion in downstream reactors. Where the initial concentration of isobutene is lower, intermediate separations may or may not be used. In some embodiments, an upstream reactor effluent may be fed to a finishing reactor, which may be a catalytic distillation reactor, providing concurrent reaction of any remaining isobutene and separation of the dimer/MTBE product from the remaining C4 components, including n-butane, isobutane, 1-butene, and 2-butene. The catalyst in the catalytic distillation reactor may also have functionality for selective hydrogenation of any butadienes present, thereby forming additional butenes.

Figure 1:
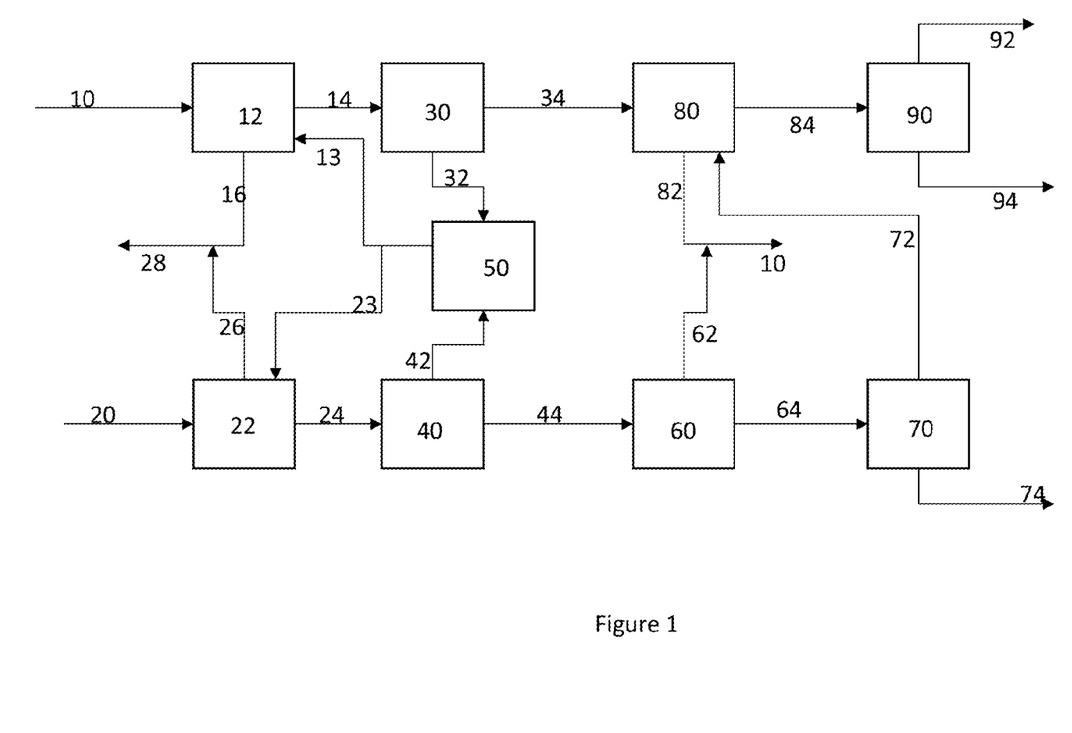
FIG. 1 is a simplified process flow diagram of a system for co-production of isobutane and 1-butene according to embodiments herein.

Referring now to FIG. 1, a simplified process flow diagram of a system for co-production of isobutane and 1-butene according to embodiments herein is illustrated. A mixed C4 stream 10, having a relatively high concentration of isobutane, such as an FCC or RFCC C4 stream, may be fed to a first reaction train 12. Reaction train 12 may be used to convert the isobutene contained therein to MTBE or isobutene dimers (iso-octene), including methanol 13 fed as a reactant or selectivator. Reaction train 12, including internal separations (not shown), may produce a Raffinate-2 stream 14, having low or no remaining isobutene, and a heavies (MTBE and/or iso-octene) stream 16.

Similarly, a mixed C4 stream 20, having a relatively low concentration of isobutane, such as a steam cracker C4 stream, may be fed to a second reaction train 22. Reaction train 22 may be used to convert the isobutene contained therein to MTBE or isobutene dimers (iso-octene), including methanol 23 fed as a reactant or selectivator. Reaction train 22, including internal separations (not shown), may produce a Raffinate-2 stream 24, having low or no remaining isobutene, and a heavies (MTBE and/or iso-octene) stream 26.

The heavies streams 16, 26 each containing MTBE or iso-octene may be combined to form a converted isobutene product stream 28. The dimers or ethers may be further processed (not shown), such as via hydrogenation or back-cracking, among other possibilities, to produce a desired product. Stream 28 may also include heavy oxygenate byproducts.

Raffinate-2 stream 14 (from first reactor train 12) may include various C4 components, such as isobutane, 1-butene, 2-butene, and n-butanes, and may be lean or absent of isobutene. Raffinate-2 stream 14 may also include methanol and/or other oxygenate byproducts, such as dimethyl ether. Raffinate-2 stream 14 may then be fed to a water wash column 30 to extract the methanol, producing a water/methanol stream 32 and a mixed C4 stream 34.

Raffinate-2 stream 24 (from second reactor train 22) may include various C4 components, such as isobutane, 1-butene, 2-butene, butadienes, and n-butanes, and may be lean or absent of isobutene. Raffinate-2 stream 24 may also include methanol and/or other oxygenate byproducts, such as dimethyl ether. Raffinate-2 stream 24 may then be fed to a water wash column 40 to extract the methanol, producing a water/methanol stream 42 and a mixed C4 stream 44.

Water/methanol streams 42, 32 may then be fed to a common methanol recovery system 50 for separation of the methanol from the water. The recovered water (not shown) may be fed back to water wash systems 30, 40, and the recovered methanol may be fed as methanol streams 13, 23 as the reactant or selectivator in reaction trains 12, 22. Fresh methanol (not show) may also be supplied within the methanol recovery system 50 or directly to the reactors where needed within reaction trains 12, 22.

Mixed C4 stream 44, having a relatively high concentration of 1-butene, may be fed to a separation system to recover a high purity 1-butene stream. The 1-butene recovery system may include a heavies column 60, separating the 1-butene from n-butane and 2-butene present. In some embodiments, a reaction zone (upstream or within the heavies column 60, not shown) may be provided to isomerize 2-butenes to 1-butene. Heavies column 60 may produce a heavy C4 stream 62, including n-butane and 2-butene, and an overhead stream 64, containing the isobutane and 1-butene. The overhead stream 64 may then be fed to a 1-butene lights column 70, where the isobutane and any dimethyl ether present may be recovered as an overheads 72, and the 1-butene may be recovered as a bottoms product 74, which may be a high purity 1-butene stream, such as having a concentration of 1-butene of greater than 90, 95, 98, or 99 wt %.

Overheads stream 72, containing isobutane from reaction train 2, and mixed C4 stream 34, having a relatively high concentration of isobutane, may be fed to a separation system to recover a high purity isobutane stream, such as having a concentration of isobutane of greater than 90, 95, 98, or 99 wt %. The isobutane recovery system may include a deisobutanizer column 80, separating the isobutane from n-butane and 2-butene present. In some embodiments, a reaction zone (upstream or within the deisobutanizer column 80, not shown) may be provided to isomerize any 1-butene present to 2-butene. Deisobutanizer column 80 may produce a heavy C4 stream 82, including n-butane and 2-butene, and an overhead stream 84, containing the isobutane. The overhead stream 84 may then be fed to a DME lights column 90, where the isobutane may be separated from any dimethyl ether present. The lights/DME may be recovered as an overheads 92, and the isobutane may be recovered as a bottoms product 94, which may be a high purity isobutane stream.

Heavy C4 streams 62, 82, including the n-butane and 2-butenes, may be combined as a heavy C4 product stream 95, for further processing or recovery, as desired. For example, the n-butane and 2-butenes may be separated to provide a high purity 2-butene stream.

Figure 2:
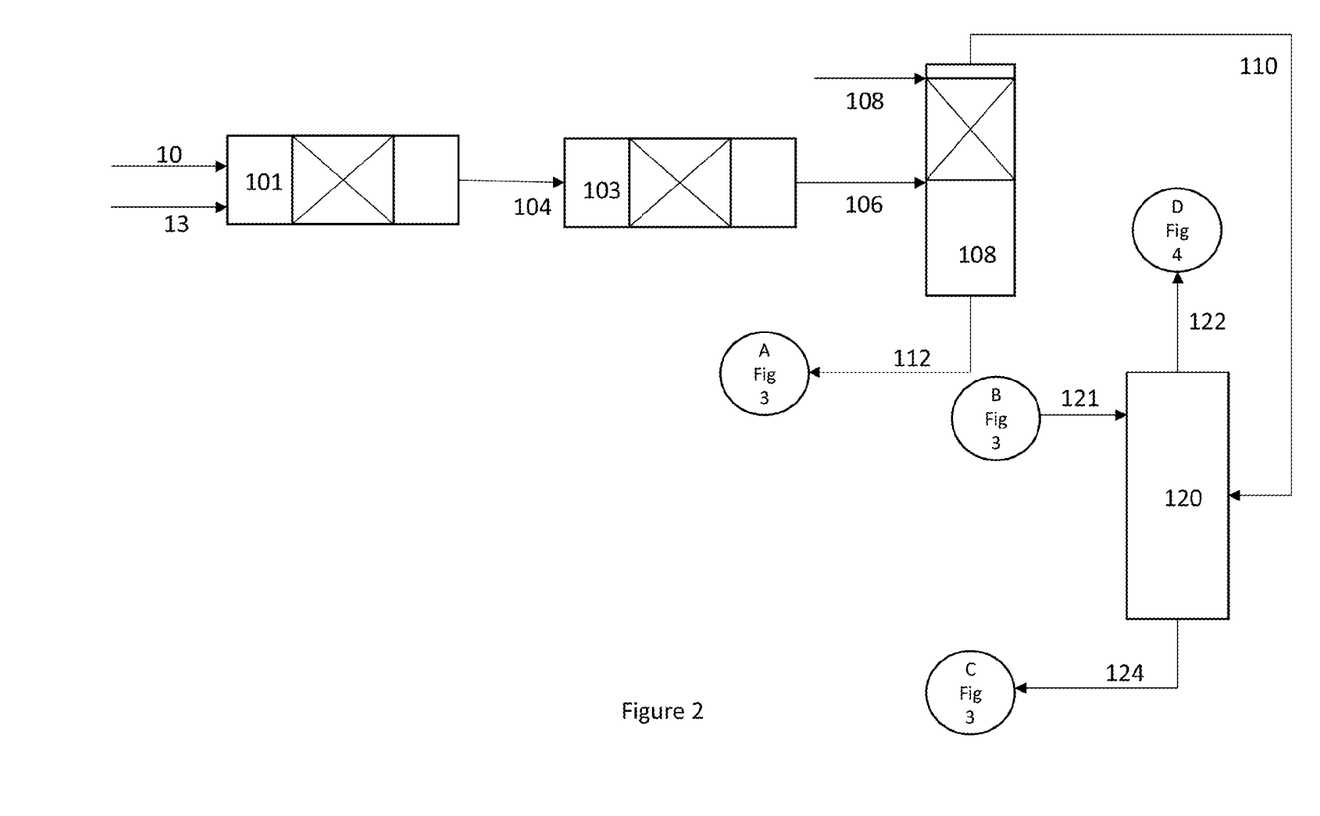
FIG. 2 is a simplified process flow diagram of a system for co-production of isobutane and 1-butene according to embodiments herein.
Figure 3:
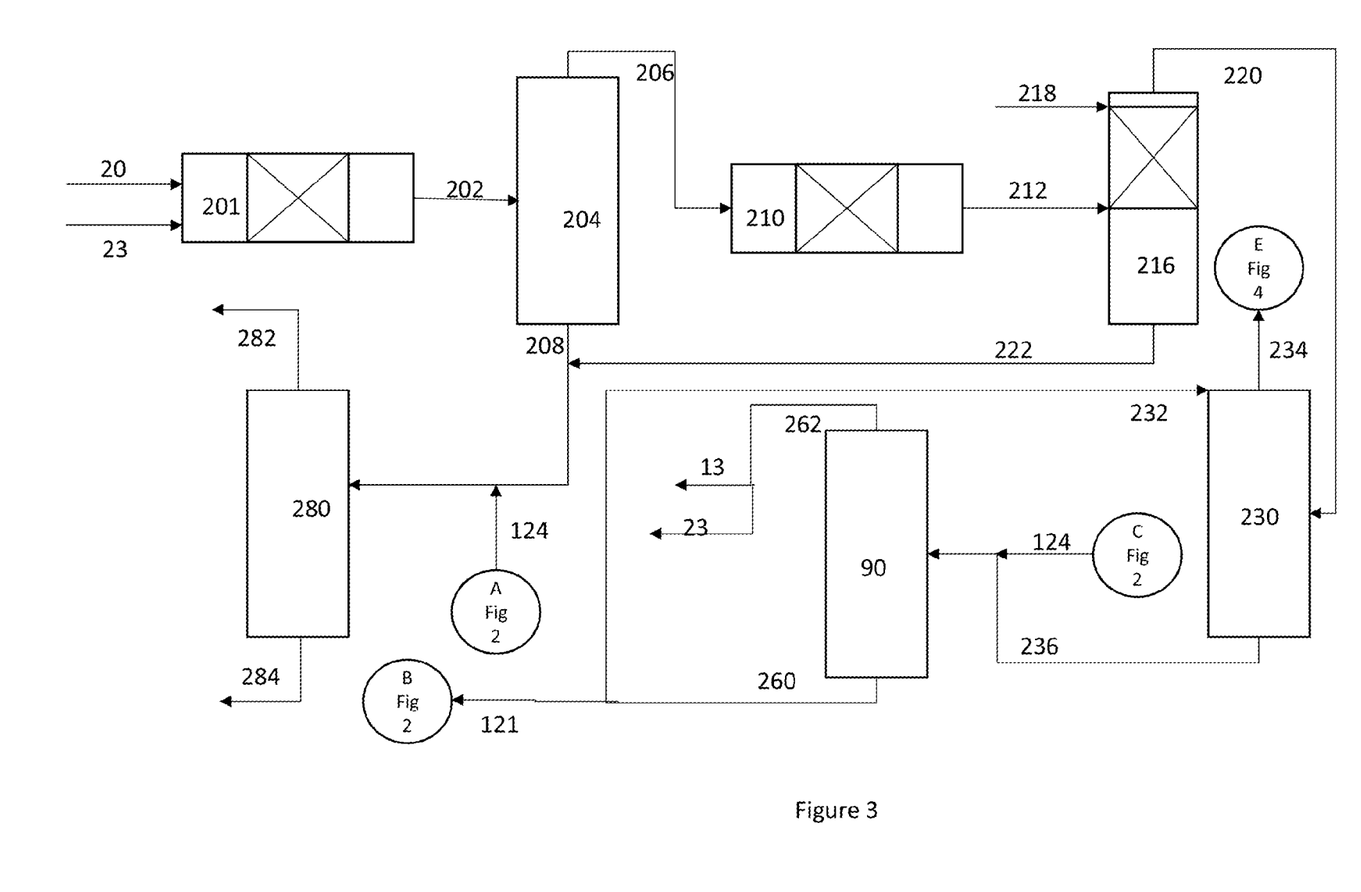
FIG. 3 is a simplified process flow diagram of a system for co-production of isobutane and 1-butene according to embodiments herein.

In some embodiments, the initial separation of the isobutene may be via dimerization or via etherification, as noted above. FIGS. 2 and 3 illustrate a simplified process flow diagram of a system in which the isobutene is separated via dimerization. While both systems achieve a similar end result, and may include similar reactors, because of the disparate feed compositions, the individual trains may be optimized for the particular feed compositions or compositional ranges expected.

Referring now to FIG. 2, a simplified process flow diagram of reaction train 1 (high isobutane content) is illustrated. The mixed C4 stream 10 and methanol 13 may be fed to dimerization reactors 101, 103, each containing a selective dimerization catalyst for converting isobutene to isobutene dimers. The effluent 104 from the first dimerization reactor 101 may be fed to the second dimerization reactor 103 for additional conversion of isobutene. The effluent 106 from the second dimerization reactor may then be fed to a catalytic distillation column 108 for additional conversion of the isobutene while concurrently separating the lighter C4 components not reacted from the desired dimer and any heavy oxygenate byproducts. Additional methanol 109 may be added to the catalytic distillation column 108, as needed. The lighter C4 components may be recovered as an overheads fraction 110, while the dimer and heavy byproducts may be recovered as a bottoms fraction 112.

Overheads fraction 110 may include isobutane, 1-butene, 2-butene, and methanol, among other components. Overheads fraction 110 may then be fed to a water wash column 120 for separation of the methanol from the C4 hydrocarbons. Wash water 121 may be fed toward the top of water wash column 120 and contacted in counter current flow with the C4 hydrocarbons to remove methanol. The C4 hydrocarbons may be recovered from the water wash column 120 as an overheads fraction 122 and the methanol/water mixture may be recovered as a bottoms fraction 124.

Referring now to FIG. 3, a simplified process flow diagram of reaction train 2 (high isobutene content) is illustrated. The mixed C4 stream 20 and methanol 23 may be fed to a first dimerization reactors 201, containing a selective dimerization catalyst for converting isobutene to isobutene dimers. The effluent 202 from the first dimerization reactor 201 may be fed to a debutanizer column 204 to separate the dimers 206 from the unreacted C4 components 208, which may be leaner in isobutene compared to feed stream 20 on a C4 basis.

Overheads fraction 208 (the unreacted C4s) may then be fed to a second dimerization reactor 210 for additional conversion of isobutene. The effluent 212 from the second dimerization reactor may then be fed to a catalytic distillation column 216 for additional conversion of the isobutene while concurrently separating the lighter C4 components not reacted from the desired dimer and any heavy oxygenate byproducts. Additional methanol 218 may be added to the catalytic distillation column 108, as needed. The lighter C4 components may be recovered as an overheads fraction 220, while the dimer and heavy byproducts may be recovered as a bottoms fraction 222.

Overheads fraction 220 may include isobutane, 1-butene, 2-butene, and methanol, among other components. Overheads fraction 220 may then be fed to a water wash column 230 for separation of the methanol from the C4 hydrocarbons. Wash water 232 may be fed toward the top of water wash column 230 and contacted in counter current flow with the C4 hydrocarbons to remove methanol. The C4 hydrocarbons may be recovered from the water wash column 230 as an overheads fraction 234 and the methanol/water mixture may be recovered as a bottoms fraction 236.

Methanol/water streams 124 (FIG. 2) and 236 may then be combined and fed to a common methanol recovery system 250. Methanol recovery system 250 may include distillative and/or membrane separations to separate the water from the methanol. As illustrated, a distillation of the water/methanol mixture may produce a bottoms water stream 260 and an overheads methanol stream 262. Water in bottoms water stream 260 may be returned to water wash columns 230, 120 (FIG. 2) via streams 232, 121, while the methanol in stream 262 may be fed to the various reactors (201, 210, 216, 101, 103, 108) as desired, such as via streams 13, 23.

In some embodiments, the heavies streams (208, 222, 124 (FIG. 2)), including dimers and any heavy oxygenate byproducts, may be combined for further processing. In some embodiments, the heavies streams may be combined and separated in a distillation column 280 to recover a dimers fraction 282 and a heavy oxygenate fraction 284, each of which may be further processed and/or used in fuel blending (such as in gasoline, diesel, etc.).

Figure 4:
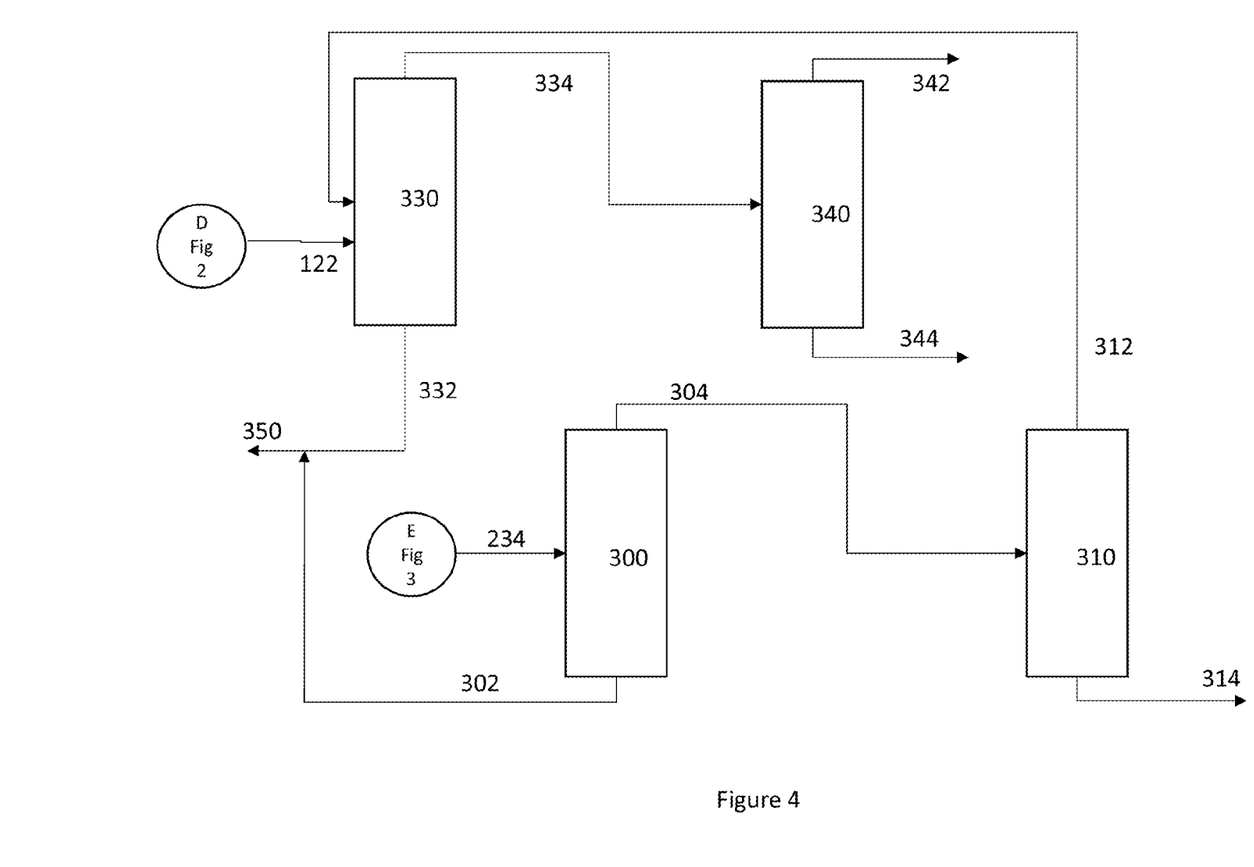
FIG. 4 is a simplified process flow diagram of a system for co-production of isobutane and 1-butene according to embodiments herein.

Following removal of the isobutene via reaction and generation of the individual Raffinate-2 streams in separate reactor trains, the mixed C4s may then be separated to result in the desired isobutane and 1-butene product streams. FIG. 4 illustrates the integrated isobutane and 1-butene purification zones, according to some embodiments herein.

Mixed C4 stream 234 having a relatively high concentration of 1-butene, may be fed to a separation system to recover a high purity 1-butene stream. The 1-butene recovery system may include a heavies column 300, separating the 1-butene from n-butane and 2-butene present. Heavies column 300 may produce a heavy C4 stream 302, including n-butane and 2-butene, and an overhead stream 304, containing the isobutane and 1-butene. The overhead stream 304 may then be fed to a 1-butene lights column 310, where the isobutane and any dimethyl ether present may be recovered as an overheads 312, and the 1-butene may be recovered as a bottoms product 314, which may be a high purity 1-butene stream.

Overheads stream 312, containing isobutane from reaction train 2, and mixed C4 stream 122, having a relatively high concentration of isobutane, may be fed to a separation system to recover a high purity isobutane stream. The isobutane recovery system may include a deisobutanizer column 330, separating the isobutane from n-butane and 2-butene present. Deisobutanizer column 330 may produce a heavy C4 stream 332, including n-butane and 2-butene, and an overhead stream 334, containing the isobutane. The overhead stream 334 may then be fed to a DME lights column 340, where the isobutane may be separated from any dimethyl ether present. The lights/DME may be recovered as an overheads 342, and the isobutane may be recovered as a bottoms product 344, which may be a high purity isobutane stream. Heavy C4 streams 302, 332, including the n-butane and 2-butenes, may be combined as a heavy C4 product stream 350.

As described above, embodiments herein may be used to efficiently produce isobutane and 1-butene products from various mixed C4 feed streams having disparate compositions.

In some embodiments, the feed to each reaction train may undergo pre-treatment. As will be described below, a first reaction train may be used to process a high isobutane content C4 stream, and a second reaction train may be used to process a low isobutane content C4 stream, with some common systems integrating the two reaction trains. The high isobutane content streams, such as an FCC or RFCC C4 stream will be fed, as described below, to Train 1, while the low isobutane content streams, such as a steam cracker C4 stream, will be fed, as described below, to Train 2.

Train 1 Feed Pretreatment

FCC/RFCC C4s may undergo feed pre-treatment in a first pre-treatment system. The unsaturated mixed $C_4$ feedstock from the upstream plant, such as an LPG plant, may be filtered and then washed in a Water Wash Column using a counter-current flow of demineralized wash water under flow control to remove most of the water-soluble impurities, such as nitriles. The top of the Water Wash Column may be equipped with a mesh pad to coalesce and remove any unseparated water. Spent wash water from the column bottoms may be sent for treatment in the refinery wastewater system.

The washed mixed C4s may then be taken overhead from the Wash Water Column and sent under pressure control to the Train 1 C4 Feed Surge Drum. The Surge Drum may also be equipped with a coalescer and water boot to remove any remaining traces of free water. In the event a small amount of non-condensable vapors accumulates in the Surge Drum, a pressure venting system with an associated nitrogen purge may be provided to dilute and vent these vapors to flare. Washed C4 feedstock may then be pumped from the Surge Drum and sent to the Train 1 Primary Reactor.

Train 2 Feed Pretreatment

The steam cracker C4s, or C4s such as a Raffinate-1 C4 feedstock from an upstream butadiene plant, may also undergo feed pre-treatment. The unsaturated Raffinate-1 $C_4$ feedstock from the upstream BD plant may be filtered and then washed in a Water Wash Column using a counter-current flow of demineralized wash water under flow control to remove most of the water-soluble impurities, such as nitriles. The top of the Water Wash Column may be equipped with a mesh pad to coalesce and remove any unseparated water. Spent wash water from the column bottoms may be sent to a wastewater system for further treatment.

The washed mixed C4s may be taken overhead from the Wash Water Column and sent under pressure control to the Train 2 C4 Feed Surge Drum. The Surge Drum may also be equipped with a coalescer and water boot to remove any remaining traces of free water. In the event a small amount of non-condensable vapors accumulates in the Surge Drum, a pressure venting system with an associated nitrogen purge may be provided to dilute and vent these vapors to flare. Washed C4 feedstock may then be pumped from the Surge Drum and sent to the Train 2 Primary Reactor.

FCC/RFCC Reaction System

In some embodiments, the FCC/RFCC reaction system includes reactors for the selective conversion of isobutene to methyl tert butyl ether, via reaction with methanol. In other embodiments, the FCC/RFCC reaction system includes reactors for the selective dimerization of isobutene to form iso-octene, where oxygenates such as methanol may be used as selectivators.

For example, the treated mixed C4 olefin feed from the Train 1 C4 Feed Surge Drum may be mixed with recycle oxygenates and fresh and recycle methanol (selectivators) and fed to a dimerization reactor, such as a Primary Tempered Water-Cooled-Tubular-Reactor (WCTR). The mixed feed stream may be pre-heated by a low pressure (LP) steam preheater. The process fluid then passes through the catalyst-filled tube side of the WCTR.

Isobutylene dimerization to iso-octene takes place in the Primary DIB (Di-isobutylene) WCTR under relatively low temperature conditions. The heat of reaction may be removed by a closed-loop tempered water system provided for the shell side of the WCTR.

Train 1 Debutanizer Column

Effluent from the Primary WCTR may then be fed to a Debutanizer Column under pressure control. The effluent may be heated via a Debutanizer Column Feed/Bottoms exchanger prior to entering the Debutanizer.

Overhead vapor from the Debutanizer (primarily C4s and methanol) is cooled, condensed, and the condensate is collected in the Debutanizer Column Overhead Drum. Distillate from the Overhead Drum is pumped under level control from the drum. A portion of the distillate is returned to the Debutanizer Column as reflux and the net distillate flow may be preheated via a LP Steam Preheater and then sent to a Secondary WCTR Reactor.

The Debutanizer bottoms stream is cooled via the Debutanizer Feed/Bottoms exchanger and then sent to a splitter column, discussed further below.

Train 1 Secondary DIB (Di-isobutylene) Reactor

The distillate stream from the Debutanizer column is combined with the oxygenate recycle, cooled via a Feed Cooler, and fed to the inlet of a Secondary Water Cooled Tube Reactor (WCTR) to enable further conversion of the isobutylene to iso-octene and other C8 olefins. The isobutylene dimerization again takes place in the Secondary WCTR under low temperature conditions. The heat of reaction is also removed by circulating water through the shell side of the reactor using a tempered water system.

Train 1 CD Reaction Column

Effluent from the Secondary WCTR flows to the CD Reaction Column via a CD Reaction Column Feed/Bottoms exchanger. The CD Reaction Column operates in similar way to a conventional distillation column and is equipped with an external reboiler and overhead condenser. The CD Reaction Column also contains trays above and below the feed inlet nozzle. CDModules (structured catalyst supports that contain catalyst) are also located in beds above the feed nozzle. The CDModules facilitate both reaction and simultaneous distillation and separate the reaction product and heavier hydrocarbons (C8+) from unreacted C4 hydrocarbons along with MTBE and other oxygenates.

Along with other C4 hydrocarbons, unreacted isobutylene distills up through the CD Reaction column from the feed point to the reaction zone inside the CDModules for conversion of isobutylene. Unreacted C4 hydrocarbons, along with excess methanol and light impurities in the feed, leaves the column as overhead distillate.

The distillate is cooled, condensed, and the condensate is collected in the CD Reaction Column Overhead Drum. Distillate from the Overhead Drum is pumped under level control from the drum. A portion of the distillate is returned to the CD Reaction Column as reflux and the net distillate flow is then cooled and sent to a Train 1 Methanol Extraction Column for Separation of the excess methanol.

Iso-octene (DIB), C8 olefins, other heavier hydrocarbons together with the oxygenates leave the CD Reaction column as the bottoms product. The bottoms product is cooled via the CD Reaction Column Feed/bottoms exchanger and then sent to the DIB/MTBE Splitter Column for separation and recovery of the oxygenates to be used as selectivators in the main reactor section. Any oxygenates purged from the overhead of the DIB/MTBE Splitter is sent to OSBL for blending in the motor gasoline (Mogas) pool.

Reactor Train 2

In some embodiments, the steam cracker C4 reaction system includes reactors for the selective conversion of isobutene to methyl tert butyl ether, via reaction with methanol. In other embodiments, the FCC/RFCC reaction system includes reactors for the selective dimerization of isobutene to form iso-octene, where oxygenates such as methanol may be used as selectivators.

When producing dimers, Train 2 may include a Primary DIB (Di-isobutylene) Reactor. The treated mixed C4 olefin feed (Raffinate-1) from the Train 2 C4 Feed Surge Drum may be mixed with recycle oxygenates and fresh and recycle methanol (selectivators). Prior to entering the Primary Tempered Water-Cooled-Tubular-Reactor (WCTR), the mixed feed stream may be pre-heated by an LP steam preheater. The process fluid then passes through the catalyst-filled tube side of the WCTR.

Isobutylene dimerization to iso-octene takes place in the Primary DIB (Di-isobutylene) WCTR under relatively low temperature conditions. The heat of reaction is removed by a closed-loop tempered water system provided for the shell side of the WCTR.

Train 2 Debutanizer Column

Effluent from the Train 2 Primary WCTR is then fed to the Train 2 Debutanizer Column under pressure control. The Effluent is heated via the Debutanizer Column Feed/Bottoms exchanger prior to entering the Debutanizer.

Overhead vapor from the Debutanizer (primarily C4s and methanol) is cooled, condensed, and the condensate is collected in the Debutanizer Column Overhead Drum. Distillate from the Overhead Drum is pumped under level control from the drum. A portion of the distillate is returned to the Debutanizer Column as reflux and the net distillate flow is preheated via a LP Steam Preheater and then sent to the Train 2 Secondary WCTR Reactor. The Train 2 Debutanizer bottoms stream may be cooled via a Debutanizer Feed/Bottoms exchanger and then sent to the MTBE/DIB Splitter column under flow control.

Train 2 Secondary DIB (Di-isobutylene) Reactor

The distillate stream from the Train 2 Debutanizer column is combined with the oxygenate recycle, and fed to the inlet of a Train 2 Secondary Water Cooled Tube Reactor (WCTR) to enable further conversion of the isobutylene to iso-octene and other C8 olefins. The isobutylene dimerization again takes place in the Secondary WCTR under low temperature conditions.

Train 2 MTBE CD Reaction Column (Including CDHydro Functionality)

Effluent from the Secondary WCTR flows to a Train 2 CD Reaction Column via the CD Reaction Column Feed/Bottoms exchanger. The CD Reaction Column operates in similar way to a conventional distillation column and is equipped with an external reboiler and overhead condenser. The CD Reaction Column also contains trays above and below the feed inlet nozzle. CDModules (structured catalyst supports that contain catalyst) are also located in beds above the feed nozzle.

The CDModules in the Train 2 CD Reaction column may facilitate both reaction (selective hydrogenation and isobutylene dimerization) and simultaneous distillation and separate the reaction product and heavier hydrocarbons (C8+) from unreacted C4 hydrocarbons along with MTBE and other oxygenates.

For Train 2, the CD Reaction column is equipped with two types of CDModules. The first type of CDModules provides catalysts to support continued dimerization of isobutylene to C8s. The second type of CDModules provides catalysts to selectively hydrogenate butadienes. These CDModules provide the exclusive CDHydro functionality. Hydrogenation also requires the injection of a small amount of fresh hydrogen into the CD Reaction column.

Three types of chemical reactions occur in the CDHydro section: hydrogenation of butadiene into n-butenes, hydroisomerization of n-butenes between 1-butene and 2-butene, and olefin saturation. Olefin saturation may be minimized with the use of highly selective catalysts and by the high reactivity of butadiene in relation to the olefins.

Selective hydrogenation is an exothermic process and therefore causes a temperature rise across the reactor. The heat of reaction is absorbed by the CD Column reflux as it passes downward through the CDModules.

Along with other C4 hydrocarbons, unreacted isobutylene and butadiene distills up through the CD Reaction column from the column feed point to the reaction zone inside the CDModules for conversion of isobutylene and saturation of dienes. Unreacted C4 hydrocarbons, along with excess methanol and light impurities in the feed, are recovered from the column as overhead distillate.

The distillate is cooled, condensed, and the condensate is collected in the Train 2 CD Reaction Column Overhead Drum. Distillate from the Overhead Drum is pumped under level control from the drum. A portion of the distillate is returned to the CD Reaction Column as reflux and the net distillate flow is then cooled and sent to a Methanol Extraction Column for Separation of the excess methanol. Non-condensables are periodically vented from the Overhead Drum using a remote HC valve.

Iso-octene (DIB, Dimer8), C8 olefins, other heavier hydrocarbons together with the oxygenates leaves the CD Reaction column as a bottoms product. The bottoms product may be cooled via a CD Reaction Column Feed/bottoms exchanger and then sent to the DIB/MTBE Splitter Column for separation and recovery of the oxygenates to be used as selectivators in the main reactor section. A portion of the oxygenates purged from the overhead of the DIB/MTBE Splitter may be sent for blending in the Mogas pool.

Dimer8 Common Methanol Recovery Section (Reaction Trains 1 & 2)

The C8 distillate streams from CD Reaction Columns in Trains 1 & 2 (containing a mixture of C4 hydrocarbons and methanol) are first treated separately in the Train 1 and Train 2 Methanol Extraction columns, as noted above. Methanol may be washed from each of the C8 distillate streams using countercurrent demineralized water flows. The Methanol Extraction Columns may each be equipped with mesh pads at the top of the columns to prevent water carry-over. Washed C8 hydrocarbons are taken overhead from each of the Train 1 and 2 to provide the individual Raffinate-2 streams.

The washed Raffinate-2 from the Train 1 Methanol Extraction Column is then fed to the Isobutane Purification Section. The washed Raffinate-2 from the Train 2 Methanol Extraction Column is then fed to the 1-Butene Recovery and Purification Section.

The aqueous extracts (bottoms) streams from the Train 1 and Train 2 Methanol Extraction columns are then combined and sent to the common Methanol Recovery Column for separation of both methanol and water by distillation. Overhead vapor from the common Methanol Recovery column is cooled, condensed and the condensate is collected in the Methanol Recovery Column Overhead Drum. Distillate from the Overhead Drum is pumped under level control from the drum. A portion of the distillate is returned to the Methanol Separation Column as reflux and the net distillate flow (purified methanol) is recycled back to the Reaction Train 1 and Train 2 Primary and Secondary Reactors and CD Reaction Columns. Fresh make-up methanol may also be added to the Overhead Drum. Wash water from the Methanol Recovery Column bottoms is recycled back to the Train 1 and Train 2 Methanol Extraction Columns for reuse.

Common Dimer8 DIB/Oxygenate Splitter Column

The bottoms streams from the Dimer8 Reaction Train 1 and Train 2 Debutanizer and CD Reaction columns may contain oxygenates such as TBA, MTBE, MSBE and C9 ethers that are removed in the DIB/Oxygenate Splitter column. These bottoms streams from Train 1 and Train 2 are combined and fed to a single DIB/Oxygenate column.

In the DIB/Oxygenate column, a majority of the lighter oxygenates (MTBE, MSBE and TBA) are distilled upwards in the vapor phase and then condensed in the overhead. The overhead vapor is water-cooled, condensed in the Splitter Condenser, and the condensate is collected in the Oxygenate/DIB Splitter Overhead drum.

Distillate from the Overhead Drum is pumped and a portion of the distillate is returned to the MTBE/DIB Splitter Column as reflux. Most of the oxygenate purge from the column is pumped back and blended with the unit feedstock to be used as selectivators in the Dimer8 Reaction Train 1 and Train 2 Primary and Secondary Reactors. A smaller portion of the distillate product is sent as an Oxygenate purge for blending in the Mogas pool. The Splitter Bottoms stream is composed of the iso-octene (DIB), other C8 olefins, C12, C16 and C9 ethers. The bottoms stream is then sent to the C8 Saturation Section to provide an iso-octane product.

Common Iso-Octene Saturation

If desired, the iso-octene recovered from the Splitter bottoms stream may be hydrogenated to form iso-octane.

Isobutane Purification (Raffinate-2 from Train 1)

The Raffinate-2 stream from Reaction Train 1 is combined with the overhead product from the B1 Lights Column (see process description for the 1-Butene Separation Unit below) and sent to the Isobutane Purification Section.

The combined Raffinate-2 feedstock is first fed to the Deisobutanizer Column. The Deisobutanizer serves to remove isobutane and light hydrocarbons from the rest of the C4s in the Raffinate 2. The net condensate flow from the Deisobutanizer column is then fed to the DME lights column. The bottoms stream from DME Lights Column is recovered as the Bottoms Product, which may include 2-butene and n-butane.

DME Lights Column

The net overhead flow from the Deisobutanizer column is then fed to the DME Lights column. The DME Lights column serves to remove light oxygenates (such as DME) and other light hydrocarbons from the high purity isobutane product. The Deisobutanizer column overhead flow may be preheated via the DME Lights column Feed/Effluent exchanger and then fed to the DME Lights column.

Overhead vapor from the DME Lights column is cooled, condensed and the condensate is collected in the DME Lights Column Overhead Drum. A portion of the distillate is returned to the DME Lights Column as reflux and the net distillate flow (DME and other light hydrocarbons) is recovered as a DME Lights product.

The bottoms flow from the DME Lights Column is cooled via the DME Lights column Feed/Effluent exchanger, further cooled via the Isobutane Product Cooler and then sent to Battery Limits as the high purity Isobutane Product. In some embodiments, the isobutane stream recovered may have a purity of at least 99 wt %. In other embodiments, the isobutane stream recovered may have a purity of greater than 99.2 wt %, greater than 99.3 wt %, greater than 99.4 wt %, or even greater than 99.5 wt %.

1-Butene Separation (Raffinate-2 from Train 2)

Raffinate-2 from Reaction Train 2 is fed to the combined B1 Heavies and B1 Lights Columns to separate and purify Butene-1 product from the rest of the raffinate-2 feed. The raffinate-2 from Dimer8 Reaction Train 1 is first fed to the B1 Heavies Column.

The compressed overhead stream from the B1 Heavies Column is partially condensed via the Reboiler for the B1 Heavies Column and the condensate is then cooled and collected in the B1 Heavies Column Reflux Drum. Condensate from the Reflux Drum is pumped and a portion of the condensate is returned to the B1 Heavies column as reflux. The net condensate flow is then fed to the B1 Lights Column.

The bottoms stream from B1 Heavies Column is pumped to Battery Limits and provides a Raffinate-3 product.

Lights Columns Section

The net condensate flow from the B1 Heavies column Reflux Drum is pumped to the B1 Lights Column section for further separation and purification of the 1-butene. The compressed overhead stream from the B1 Lights Column is partially condensed via the Reboiler for the B1 Lights Column and the condensate is then water cooled and collected in the B1 Lights Column Reflux Drum. Condensate from the Reflux Drum is pumped and a portion of the condensate is returned to the B1 Lights column as reflux. The net (isobutane rich) condensate flow is then combined with the Raffinate 2 from Train 1 and processed in the Isobutane Purification Section, as described above.

The bottoms stream from B1 Lights Column is the high purity butene-1 product. In some embodiments, the 1-butene stream recovered may have a purity of at least 99 wt %. In other embodiments, the 1-butene stream recovered may have a purity of greater than 99.2 wt %, greater than 99.3 wt %, greater than 99.4 wt %, or even greater than 99.5 wt %.

As described above, embodiments herein may provide for the efficient co-production of both high purity 1-butene and high purity isobutane. The compositions of the initial mixed C4 streams is advantageously utilized, with partial common processing where it is advantageous, to produce the high purity products. Maintaining the reaction trains and water wash as separate systems enables the production of high quality and high purity isobutane and 1-butene streams.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the co-production of high purity isobutane and high purity 1-butene streams, the process comprising:
    providing a first mixed $C_4$ stream and a second mixed $C_4$ stream, each comprising isobutene, isobutane, 1-butene, and 2-butene, and wherein the first mixed $C_4$ stream has a higher concentration of isobutane than the second mixed $C_4$ stream;
    feeding the first mixed $C_4$ stream and methanol, as a reactant or selectivator, to a first reaction system for converting isobutene contained therein to methyl tert butyl ether or isobutene dimers;
    feeding the second mixed $C_4$ stream and methanol, as a reactant or selectivator, to a second reaction system for converting isobutene contained therein to methyl tert butyl ether or isobutene dimers;
    separating an effluent from the first reaction system in a first separation system, including a water wash system, to recover a first lights stream comprising 1-butene, 2-butene, isobutane, a first methanol+water stream, and a first heavy stream comprising the methyl tert butyl ether or the isobutene dimers;
    separating an effluent from the second reaction system in a second separation system, including a water wash system, to recover a second lights stream comprising 1-butene, 2-butene, and isobutane, a second methanol+water stream, and a second heavy stream comprising the methyl tert butyl ether or the isobutene dimers;
    feeding the first and second methanol+water streams to a methanol recovery system to separate methanol from the water and returning at least a portion of the methanol to either or both the first and second reaction systems;
    feeding the second lights stream to a separation system for recovering an isobutane containing stream, a 1-butene stream, and a first heavy $C_4$ stream comprising n-butanes and 2-butene;
    feeding the isobutane containing stream and the first lights stream to a separation system for recovering an isobutane stream and a second heavy $C_4$ stream comprising n-butanes and 2-butene.

2. The process of claim 1, further comprising separating dimethyl ether from the isobutane stream.

3. The process of claim 1, wherein the isobutane stream has a purity of at least 99 wt % and wherein the 1-butene stream has a purity of at least 99 wt %.

4. The process of claim 1, further comprising feeding a hydrocarbon stream to a fluid catalytic cracking process or a residue fluid catalytic cracking process and recovering the first mixed $C_4$ stream, wherein the first mixed $C_4$ stream has a concentration of isobutane of at least 20 wt %.

5. The process of claim 4, further comprising feeding a hydrocarbon stream to a steam cracking process and recovering the second mixed $C_4$ stream, wherein the second mixed $C_4$ stream has a concentration of isobutane of less than 5 wt %.

6. The process of claim 5, wherein the first mixed $C_4$ stream has a concentration of isobutene of less than 25 wt %, and wherein the second mixed $C_4$ stream has a concentration of isobutene of at least 30 wt %.

7. A system for the co-production of high purity isobutane and high purity 1-butene streams, the system comprising:
    a first mixed $C_4$ stream and a second mixed $C_4$ stream, each comprising isobutene, isobutane, 1-butene, and 2-butene, and wherein the first mixed $C_4$ stream has a higher concentration of isobutane than the second mixed $C_4$ stream;
    a first methanol stream and a second methanol stream;
    a first reaction system configured to receive the first mixed $C_4$ stream and the first methanol stream and to react the first mixed $C_4$ stream and methanol, as a reactant or selectivator, converting isobutene contained therein to methyl tert butyl ether or isobutene dimers;
    a second reaction system configured to receive the second mixed $C_4$ stream and the second methanol stream and to react the second mixed $C_4$ stream and methanol, as a reactant or selectivator, converting isobutene contained therein to methyl tert butyl ether or isobutene dimers;
    a first separation system, including a water wash system, for separating an effluent from the first reaction system to recover a first lights stream comprising 1-butene, 2-butene, isobutane, a first methanol+water stream, and a first heavy stream comprising the methyl tert butyl ether or the isobutene dimers;
    a second separation system, including a water wash system, for separating an effluent from the second reaction system to recover a second lights stream comprising 1-butene, 2-butene, isobutane, a second methanol+water stream, and a second heavy stream comprising the methyl tert butyl ether or the isobutene dimers;
    a common methanol recovery system for receiving the first and second methanol+water streams to separate methanol from the water and a flow line for returning at least a portion of the methanol to either or both the first and second reaction systems;

a first lights separation system for receiving the second lights stream and recovering an isobutane containing stream, a 1-butene stream, and a first heavy $C_4$ stream comprising n-butanes and 2-butene;

a second lights separation system for receiving the first lights stream and for recovering an isobutane stream and a second heavy $C_4$ stream comprising n-butanes and 2-butene.

8. The system of claim 7, further comprising a first mixer for mixing the first and second heavy $C_4$ streams, and a second mixer for mixing the first and second heavy streams.

9. The system of claim 7, wherein each of the first and second reaction systems is configured to produce isobutene dimers.

10. The system of claim 7, wherein each of the first and second reaction systems is configured to produce methyl tert butyl ether.

11. The system of claim 7, wherein the first reaction system includes a fixed bed reactor, or two or more fixed bed reactors in series or in parallel, followed by a catalytic distillation reactor.

12. The system of claim 7, wherein the second reaction system includes a fixed bed reactor, or two or more fixed bed reactors in series or in parallel, followed by a catalytic distillation reactor.

* * * * *